(12) United States Patent
Petersen et al.

(10) Patent No.: US 9,222,117 B2
(45) Date of Patent: Dec. 29, 2015

(54) LEUCINE-RICH PEPTIDE COMPOSITIONS AND METHODS FOR ISOLATION

(71) Applicants: Brent Petersen, Twin Falls, ID (US); Loren S. Ward, Twin Falls, ID (US); Eric D. Bastian, Twin Falls, ID (US); Stanley Wrobel, Simpsonville, SC (US)

(72) Inventors: Brent Petersen, Twin Falls, ID (US); Loren S. Ward, Twin Falls, ID (US); Eric D. Bastian, Twin Falls, ID (US); Stanley Wrobel, Simpsonville, SC (US)

(73) Assignee: Glanbia Nutritionals (Ireland) Ltd., Kilkenny (IE)

( * ) Notice: Subject to any disclaimer, the term of this patent is extended or adjusted under 35 U.S.C. 154(b) by 0 days.

(21) Appl. No.: 14/188,676

(22) Filed: Feb. 24, 2014

(65) Prior Publication Data

US 2014/0171378 A1 Jun. 19, 2014

Related U.S. Application Data

(62) Division of application No. 12/411,772, filed on Mar. 26, 2009, now abandoned.

(60) Provisional application No. 61/039,426, filed on Mar. 26, 2008.

(51) Int. Cl.
*C12P 21/06* (2006.01)
*A23L 1/305* (2006.01)
*A61K 38/01* (2006.01)

(52) U.S. Cl.
CPC ............... *C12P 21/06* (2013.01); *A23L 1/3051* (2013.01); *A23L 1/3053* (2013.01); *A61K 38/018* (2013.01)

(58) Field of Classification Search
None
See application file for complete search history.

(56) References Cited

U.S. PATENT DOCUMENTS

| 4,940,662 | A | 7/1990 | Yamazaki et al. |
| 6,221,423 | B1 * | 4/2001 | Cho et al. ............ 426/656 |
| 2004/0067279 | A1 | 4/2004 | Delest et al. |
| 2005/0256057 | A1 | 11/2005 | Edens et al. |
| 2007/0054352 | A1 | 3/2007 | van der Burg-Koorevaar et al. |
| 2009/0105123 | A1 * | 4/2009 | Tisdale et al. ............ 514/4 |
| 2014/0171378 | A1 * | 6/2014 | Petersen et al. ............ 514/21.92 |

FOREIGN PATENT DOCUMENTS

| AU | 2009228250 | * | 7/2013 |
| EP | 2274002 B1 | * | 1/2011 |
| JP | 5750039 | * | 5/2015 |
| WO | WO9965326 | | 12/1999 |
| WO | WO0190144 | | 11/2001 |
| WO | WO0271854 | | 3/2002 |
| WO | WO02071854 | | 9/2002 |
| WO | WO 2007064618 | * | 6/2007 |

OTHER PUBLICATIONS

Frazzetti. Tetrahedral aminopeptidase: a novel large protease complex from archaea.EMBO J. May 1, 2002;21(9):2132-8 http://www.ncbi.nlm.nih.gov/pubmed/11980710 (abstract).*
Leroy et al. Effects of commercial enzymes on the adhesion of a marine biofilm-forming bacterium. Biofouling vol. 24, No. 1 Jan. 2008, pp. 11-22.
Van Amersfoort et al. Receptors, mediators, and mechanisms involved in bacterial sepsis and septic shock. Clin Microbiol Rev vol. 16, No. 3, Jul. 2003, p. 379-414.

* cited by examiner

*Primary Examiner* — Maury Audet
(74) *Attorney, Agent, or Firm* — Donna J. Russell

(57) ABSTRACT

Disclosed are compositions comprising isolated peptides having a leucine content of from about 12 to about 40 weight percent. Also disclosed is a method for isolating leucine-rich peptides from protein sources such as bovine whey and methods of use for these peptides to provide beneficial effects in a human and/or animal such as increasing blood flow, decreasing blood pressure, increasing muscle mass, improving cognitive function, improving cardiovascular function, etc.

5 Claims, No Drawings

LEUCINE-RICH PEPTIDE COMPOSITIONS AND METHODS FOR ISOLATION

CROSS-REFERENCE TO RELATED APPLICATIONS

This application is a divisional application from U.S. patent application Ser. No. 12/411,772, filed Mar. 26, 2009, which claimed the benefit of priority of earlier-filed U.S. provisional patent application No. 61/039,426, filed Mar. 26, 2008.

FIELD OF THE INVENTION

The invention relates to dietary peptide compositions for stimulating protein synthesis, decreasing protein degradation, producing vasodilation, increasing nitric oxide production, and decreasing blood flow. More specifically, the invention relates to leucine-rich peptide compositions and methods for their isolation from proteins.

BACKGROUND OF THE INVENTION

Loss of muscle tissue often occurs as a result of aging, malnutrition, and catabolic diseases such as burns, sepsis, and cancer. Dietary protein supplementation may be beneficial, but supplementation with the essential amino acid leucine has been shown to be especially beneficial. Dietary leucine has, for example, recently been shown to suppress the rate of myofibrillar protein degradation and muscle weight loss in rats. Leucine also stimulates muscle protein synthesis and modulates the activity of various proteins involved in the control of mRNA translation. Leucine may stimulate protein synthesis directly or through its metabolite, α-ketoisocaproic acid. Leucine may stimulate translation either independently or by interaction with the mammalian target of rapamycin (mTOR).

Leucine is one of the branched-chain amino acids and is an essential amino acid. It is the only amino acid that is converted to acetyl-coenzyme A and alpha-ketoacids and is an important source of nitrogen for synthesis of glutamine. In addition to its effects on protein synthesis and degradation, leucine also stimulates glucose uptake by protein kinase C (PKC), while insulin modulates glucose uptake via protein kinase B.

Milk-derived whey is one good source of muscle-building proteins. Whey protein isolates and whey protein concentrates are used in protein-building dietary supplements. Whey proteins are a good source of leucine, but for many individuals who need the muscle-building amino acids dietary proteins can provide, it is difficult to digest and/or absorb proteins. It is therefore important to find ways to provide leucine-containing amino acid compositions that provide amino acids in a more bioavailable form for improving muscle protein synthesis.

SUMMARY OF THE INVENTION

The present invention relates to peptides having a leucine content of from about 12% to about 40% ("leucine-rich peptides"), those peptides being isolated from a protein source by a method comprising the steps of hydrolyzing the protein in the presence of one or more leucyl aminopeptidases, optionally in combination with additional proteases, to produce a protein hydrolysate, deactivating the enzymes, and filtering the protein hydrolysate to provide a permeate comprising peptides having a molecular weight of from about 200 to about 4,000, including sub-ranges in-between, such as, for example, a molecular weight of from about 200 to about 1,000 or a molecular weight of from about 400 to about 1,000. Optionally, the step of concentrating the leucine-rich peptides by removing the aqueous fluid from the permeate may be added. Also disclosed are method of use of such peptides for a variety of beneficial effects, such as producing vasodilation, increasing nitric oxide production, decreasing blood pressure, increasing blood flow, increasing muscle tissue, improving wound healing, and improving cognitive function.

The invention also relates to a method for isolating leucine-rich peptides from a protein source, the method comprising the steps of hydrolyzing the protein in the presence of one or more leucyl aminopeptidases, optionally in combination with additional proteases, to produce a protein hydrolysate, deactivating the enzymes, filtering the protein hydrolysate to provide a permeate, and concentrating the permeate containing the leucine-rich peptides.

In various embodiments, the protein may be derived from animal or plant sources, including, for example, legumes such as soy or pea, fish, meat, milk, blood, egg, corn, wheat gluten, maize, or combinations thereof. In some embodiments, the protein source may be bovine milk, bovine whey, whey protein concentrates, and/or whey protein isolates.

In various embodiments, the leucine content of the leucine-rich peptides may be within various subranges of the about 12 to about 40 percent range, such as, for example, from about 12 to about 30 weight percent leucine, from about 15 to about 20 weight percent leucine, from about 15 to about 25 weight percent leucine, and from about 20 to about 25 weight percent leucine.

DETAILED DESCRIPTION

The inventors have discovered that peptides having a leucine content of from between about 12% and about 40% ("leucine-rich peptides") may be isolated from a protein source by a method comprising the steps of hydrolyzing the protein in the presence of one or more (i.e., at least one) leucyl aminopeptidases, optionally in combination with additional proteases, to form a protein hydrolysate, deactivating the enzymes, filtering the protein hydrolysate to isolate leucine-rich peptides, and concentrating the leucine-rich peptides. In one embodiment, the method comprises hydrolyzing the protein in the presence of one or more aminopeptidases which may act as leucyl aminopeptidases (leucine aminopeptidases), optionally supplemented with additional proteases, to form a protein hydrolysate, deactivating the enzymes, filtering the protein hydrolysate using ultrafiltration, nano-filtration, or another suitable filtration method to give a permeate containing the leucine-rich peptides, and concentrating the leucine-rich peptides in the permeate using reverse osmosis, evaporation, or another suitable method for concentrating the peptides by removing the aqueous portion of the permeate from the filtration step. The invention also provides compositions comprising leucine-rich peptides prepared by the method.

Dietary leucine appears to have a number of beneficial effects, including stimulation of muscle protein synthesis and suppression of the rate of myofibrillar protein degradation and muscle weight loss. Leucine also increases hypothalamic mTOR signaling and decreases food intake and body weight (Cota, D. et al. *Science* (2006) 312: 927-930). Leucine administration increases leptin levels, and leptin is known to promote lipolysis in adipose tissue, but has no apparent effect on lean tissue. Increased leptin levels result in decreased hunger, decreased food consumption, and increased cellular energy expenditure.

Protein sources such as standard whey protein hydrolysates may contain as much as 10% leucine, but given the variety of beneficial effects of this amino acid and the fact that it is not synthesized in the body from other amino acids, it has been a goal of the food and nutritional supplement industry to develop ways to increase leucine levels in order to promote its beneficial effects, especially its effects on muscle building and inhibition of muscle wasting. The present invention provides amino acid compositions that are rich in leucine and such compositions may be isolated from readily-available protein sources using the method of the invention.

The inventors proposed to use leucine aminopeptidase to process whey proteins to produce bioactive/bioavailable leucine-containing peptides which they have demonstrated to have a variety of desirable effects. Leucine residues appear to play an important role in the distinction between the effects of remarkably similar proteins. For example, Angiotensin I differs from Angiotensin II by two additional carboxyl-terminal amino acids—histidine and leucine. Met-enkephalin, a neuropeptide, has many similar effects to those of Leu-enkephalin, which appear to be mediated by the aromatic side-chains of the amino acids in the peptides. Both peptides consist of 5 amino acid residues. Met-enkephalin and Leu-enkephalin differ, however, in the carboxyl-terminal fifth amino acid residue. In Met-enkephalin, it is methionine. In Leu-enkephalin it is leucine. Both appear to have effects on arterial blood pressure and vasodilation, but in this area the amino acid difference appears to be more significant, with Leu-enkephalin appearing to have a stronger effect (Moore, R. H. and D. Dowling, "Effects on Intravenously Administered Leu- or Met-Enkephalin on Arterial Blood Pressure," *Regulatory Peptides* (1980) 1(2): 77-87). While others have provided hydrolysates containing a significant percentage of leucine present as a free amino acid (see, for example, U.S. Pat. No. 6,875,456 to Delest, V. et al.), the present invention provides small peptides (e.g., a hydrolysate containing a significant percentage of di- and tri-peptides) to deliver leucine in a more bioavailable/bioactive form. These peptides have demonstrated surprising beneficial results, such as potent inhibition of angiotensin converting enzyme (ACE) inhibition, vasodilation, and stimulation of increased nitric oxide production. Experiments demonstrate that the peptides of the invention provide bioavailable/bioactive leucine, supplementation with the peptides demonstrating many of the same beneficial effects as those provided by leucine supplementation, but with additional benefits not previously described as the result of leucine supplementation.

Leucine-rich peptide compositions of the present invention provide leucine in combination with other amino acids, but provide increased amounts of leucine in relation to the other amino acids. These compositions may readily be added as a powder to a drink formulation, to a food product, to a nutritional supplement composition such as a tablet, capsule, or other formulation, or to a pharmaceutical preparation, for example. Additional flavorings, carbohydrates, fats, proteins, vitamins, minerals, and other suitable food or supplement ingredients may be included in such compositions.

Peptides of the invention may be used to provide compositions that provide a benefit to a human or animal in areas including, but not limited to, cardiac health, sarcopenia, endothelial function, maintaining healthy blood pressure or lowering blood pressure, vasodilation, muscle growth and development, sports nutrition, infant nutrition, prevention or treatment of metabolic syndrome, cognitive function, eye health, diabetes, improvement in glycemic index, mTOR activation, wound healing, and skin care/treatment of skin disorders.

Studies have shown that human athletes given branched-chain amino acids (BCAA) before and during exercise performed better on complex cognitive tests following exercise (Hassmen, P. et al., *Nutrition* (1994) 10:405-10). When tested in dogs, BCAA supplementation appeared to be especially effective at improving cognitive performance during exercise in older dogs (Fretwell, L. et al. *J. Nutr.* (2006) 136: 2069S-2071S). Compositions of the present invention provide increased levels of the branched-chain amino acid (BCAA) leucine, in conjunction with other amino acids in a form that may be readily incorporated into tablets, capsules, food products such as, for example, nutrition bars, supplements in the form of powders, drink mixes, and other compositions for human and/or animal consumption. These compositions may provide a benefit for those individuals who desire to improve their cognitive performance. Studies performed with the peptides of the invention have demonstrated that supplementation with leucine-rich peptides promotes vasodilation and increases blood flow, as well as increasing the rate at which glucose is delivered to the tissues. Older individuals, students, and others may derive a particular benefit from foods, drinks, and/or supplements comprising leucine-rich peptides of the invention.

Metabolic syndrome (Syndrome X) is a chronic disease that affects at least 1 in every 5 adults in the United States. It is often associated with obesity, but the defining characteristic is abnormal glycemic control (glucose intolerance, insulin resistance). Protein-rich diets, especially those comprising significant amounts of leucine, are beneficial for the treatment of obesity and for the treatment of the metabolic syndrome (Layman, D. K. and D. A. Walker, *J. Nutr.* (2006) 136: 319S-323S). Compositions of the present invention provide an excellent means by which the necessary amino acids and the higher amounts of leucine necessary to affect weight management and the metabolic syndrome may be provided to a human or animal. Products such as "protein water" (water containing whey protein isolate in combination with sweeteners and flavorings), for example, may provide an additional benefit if peptides of the present invention are used as the protein component. Snack foods, nutrition bars, drinks, drink mixes, and other products may also be formulated with the leucine-rich peptides to provide compositions for use in weight management and loss of fat. Leucine-rich peptide compositions may be used to promote weight loss by incorporating those compositions into one or more food products, or may be similarly used by incorporating them into a nutritional supplement or nutritional drink for ingestion at mealtime. Between-meal-snacks may also be formulated with leucine-rich peptide compositions to decrease hunger and food consumption.

Leucine-rich peptides of the invention may be added to whey compositions, whey protein isolates, whey protein concentrates, and other protein sources to improve muscle synthesis, decrease muscle breakdown, decrease hunger and food consumption, improve blood flow, and increase nitric oxide production in the blood vessels, for example. These effects may be beneficial for a large population of individuals, including those who voluntarily wish to build additional muscle mass, those who are losing muscle mass through the process of aging and/or injury, disease (e.g., sepsis, cancer) or malnutrition, and those who desire to decrease the percentage of adipose tissue to muscle mass in the body.

Leucine-rich peptide compositions of the present invention are especially beneficial for aging individuals or others with sarcopenia. During the aging process and beginning at about age 45, human muscle mass decreases. The frailty that is associated with aged individuals may be attributed in large part to this loss of muscle mass, and that predisposes those individuals to further disease or injury. Some of the muscle tissue loss in older individuals may also be the result of malnutrition—especially in terms of protein ingestion, as protein-rich foods may tend to be more expensive and less readily available to individuals on fixed incomes. Compositions of the present invention provide nutritional supplements with which to address the needs of individuals in whom aging or malnutrition has induced muscle loss.

Body-building involves the combination of nutritional supplementation and exercise to increase muscle mass. Compositions of the present invention are ideally suited for body-building nutritional supplements. Leucine-rich compositions stimulate muscle synthesis while generally decreasing the desire to overeat and gain fat tissue. Furthermore, dietary leucine supplementation has been shown to significantly improve endurance performance (Crowe, M. J. et al., *Eur. J. Appl. Physiol.* (2006) 97(6): 664-72).

Leucine has demonstrated cardioprotective effects, in addition to its many other beneficial effects. For example, leucine protects heart muscle against myocardial ischemia and some researchers believe it is also an anti-arrhythmic factor (Gabrys, J. et al. (2002) *Pharmacology Reviews and Communications* 12: 101-108). Peptides of the present invention have been shown to act as potent angiotensin converting enzyme (ACE) inhibitors. For example, European Patent Number 1794189B1 (De Slegte, J et al.) proposes that ACE-inhibitory peptides demonstrating the greatest efficacy to date are those containing a significant percentage of proline residues. Those inventors discuss the products of companies such as Calpis and Valio, which provide tripeptides having two proline residues per tripeptide. Reporting the results of their own peptide preparation in terms of ACE inhibition (which is expressed as an IC50 value—the concentration of peptide or hydrolysate needed to reduce ACE activity by 50%), they indicate that their hydrolysate produces an IC50 (expressed as μg/ml) of 7.2. Leucine-enriched peptides of the present invention, however, have demonstrated IC50 values of from about 4.0 μg/ml to about 9.6 μgrams/ml, with an ACE-inhibitory value of from 4.0 to 4.7 being the norm for large-scale production lots.

Peptides of the present invention have also demonstrated effectiveness in producing vasodilation, increased blood flow, and increased nitric oxide (NO) production in the blood vessels (see Example 1). This combination of effects clearly demonstrates the positive effects of peptides of the invention on the cardiovascular system, and therefore illustrates the benefits of peptides of the invention as cardio-protective compositions and compositions for improving vascular function, increasing blood flow, decreasing blood pressure, increasing endurance capacity, etc. Compositions of the invention may be provided or consumed as dietary supplements and/or pharmaceutical compositions for maintaining healthy blood pressure levels and for decreasing blood pressure in individuals who have or are predisposed to elevated blood pressure levels. Such compositions may be especially beneficial for individuals who are diabetic, for example, who may have or be predisposed to high blood pressure and who may also need the increased blood flow to tissues in order to decrease tissue damage, especially in the extremities.

Leucine supplementation has been determined to be more beneficial than is generic supplementation with BCAAs for burn, trauma, and sepsis patients (DeBandt, J. and L Cynober, *J. Nutr.* (2006) 136: 308S-313S). Furthermore, leucine has an anabolic effect on proteins in skin wounds and muscle, provided that adequate additional amino acids are available. When compared with leucine supplementation alone, leucine supplementation in conjunction with protein supplementation provided a greater benefit for wound healing (Zhang, X. et al., *J. Nutr.* (2004) 134: 3313-8). Compositions of the present invention provide peptides having enhanced leucine content and are therefore excellent food, pharmaceutical, or nutritional compositions for administration to patients with burns or other skin wounds, muscle injury, trauma, sepsis, and other conditions in which the beneficial effects of leucine may be enhanced by providing leucine in combination with peptides or proteins. These compositions may be provided in oral form, via intravenous means, or by injection. Leucine-rich peptide compositions may also be used either orally or topically to enhance skin tone and suppleness, and to promote overall skin health.

Leucine-rich peptides may also provide a benefit for blood pressure regulation and inhibition of angiotensin converting enzyme (ACE). For individuals desiring to better manage blood pressure and increase blood flow to tissues, leucine-rich peptides of the invention may be consumed in food products, drinks and drink mixes, as food supplements such as tablets, capsules, powders, and other formulations that may be easily self-administered at or between mealtimes. By increasing blood flow and promoting vasodilation and nitric oxide production, compositions of the invention may provide a benefit by increasing microcirculation, promoting endothelial health, and improving nutrient delivery to the tissues. These effects may be especially important in individuals suffering from diabetes, peripheral artery disease, and other diseases affecting circulation, as well as the elderly, athletes, individuals recovering from surgery, traumatic injury, burns, chronic wounds, and other conditions where increased blood flow and nutrient delivery may promote improved health.

A variety of beneficial effects have been associated with nitric oxide production. NO relaxes smooth muscle and inhibits vascular inflammation, inhibiting endothelial cells lining the blood vessels from releasing inflammatory substances. NO inhibits smooth muscle cell migration and proliferation and decreases platelet adherence and aggregation. These effects may be especially beneficial in those predisposed to the development of atherosclerosis and to stroke, autoimmune disease, etc. NO appears to regulate vascular inflammation in part by inhibiting exocytosis of Weibel-Palade bodies, which can be triggered by thrombin, histamine, fibrin, complement, leukotrienes, and ATP, for example (Matsushita, K. et al. *Cell* (2003) 115: 139-150). Leucine-rich peptides of the present invention have been shown in vivo to increase nitric oxide production and vasodilation. Compositions of the invention may therefore provide a benefit by preventing the development of atherosclerotic lesions, decreasing vascular inflammation, decreasing platelet adherence and aggregation, etc. Compositions of the invention may therefore provide supplements that provide a significant benefit in strengthening the cardiovascular system, decreasing inflammation in the circulatory system, preventing the development of plaques in the blood vessels, and providing a more "heart-healthy" environment within the blood vessels in general.

The method may be used to isolate leucine-rich peptides from any source comprising leucine-containing proteins. Such sources may include, but not be limited to, wheat gluten, maize/corn protein isolates, egg proteins, soy and other legume proteins (e.g., pea), fish, meat, blood/blood proteins, and milk proteins. One especially valuable source of leucine-rich peptides is milk-derived whey, such as, for example, bovine milk-derived whey, whey protein isolates, and/or whey protein concentrates. Whey protein isolates generally have a protein content of at least about 90 weight percent, while whey protein concentrates may have from at least about 35 weight percent to about 80 weight percent protein.

Enzyme sources for the method of the invention may be readily identified by those of skill in the art. Leucyl aminopeptidases (leucine aminopeptidases), for example, are exopeptidases which hydrolyze the peptide bond adjacent to a free amino group and react most rapidly with leucine-containing peptides and proteins.

Using filtration, molecules are selectively passed through or transported across a membrane, and this process may be even more effective when a pressure gradient is used. Filtration is particularly effective at isolating the leucine-rich peptides. Methods of filtering molecules based upon molecular weight and other properties are known to those of skill in the art and include membrane filtration generally, ultrafiltration, and nano-filtration, for example. At this point, the isolated leucine-rich peptides are generally contained within a permeate, which is fairly low in solids. The percentage of solids in the composition (permeate) may be increased by removal of liquid (aqueous fluid). This may be done by means known to those of skill in the art, including but not limited to processes such as evaporation and reverse osmosis.

Throughout this disclosure, where the term "comprising" is used, it is intended that this term may be substituted with "consisting of" and/or "consisting essentially of," as well. The invention may be further described by means of the following non-limiting examples:

EXAMPLES

Example 1

Production of Leucine Peptides

A high protein, low fat, low lactose liquid whey protein isolate product was used as the beginning substrate. This product was pumped into reaction tanks at a solids level of 17%. The temperature was raised to 45° C. and pH adjusted to 7.3 with sodium hydroxide. A blend of proteases and aminopeptidases (e.g., leucine aminopeptidase) was then added at a level of 0.35% of the solids. Hydrolysis was allowed to proceed for a 6-hour period with hourly pH adjustments to maintain the pH at 7.3. The enzymes were then deactivated by heating the solution to 65° C.

Fractionation was performed using filtration, the hydrolysate being passed through the filter to retain molecules having a molecular weight of greater than 20,000. The permeate coming from filtration system contained the leucine peptides, having approximately 52% of the peptides in the molecular weight range of less than 1,000; 41% of the peptides in the molecular weight range of 1,000 to 4,000; and 6% of the peptides in the molecular weight range of 4,000 to 20,000. These peptides were further concentrated using reverse osmosis. The final product was then dried and packaged.

Analysis of six preparations (lots) of peptides of the invention is shown in Table 1, where Lot 06-187, Lot 06-257, and Lot 06-259 are small-scale lots and Lot 07-041, Lot 07-046, and 07-055 are large-scale production lots. The degree of hydrolysis of each lot is shown on the bottom row, with a range of hydrolysis of from about 30% to about 50% producing the desired peptides in these experiments. ACE inhibition is shown as the amount of peptide needed to produce 50% ACE inhibition.

TABLE 1

|  | Lot 06-187 | Lot 06-257 | Lot 06-259 | Lot 07-041 | Lot 07-046 | Lot 07-055 |
| --- | --- | --- | --- | --- | --- | --- |
| Tryptophan | 1.52 | 1.52 | 1.45 | 1.34 | 1.42 | 1.37 |
| Cystine | 0.90 | 1.48 | 1.25 | 0.63 | 0.51 | 0.54 |
| Methionine | 3.84 | 4.47 | 5.19 | 5.43 | 4.95 | 5.21 |
| Aspartic Acid | 8.23 | 8.52 | 7.76 | 5.92 | 5.49 | 5.63 |
| Threonine | 7.14 | 8.60 | 8.75 | 10.77 | 10.33 | 11.08 |
| Serine | 4.31 | 4.36 | 4.10 | 4.78 | 4.38 | 4.43 |
| Glutamic Acid | 13.43 | 13.42 | 12.20 | 8.78 | 8.34 | 8.47 |
| Proline | 4.23 | 4.79 | 3.97 | 2.26 | 2.28 | 2.37 |
| Glycine | 1.70 | 1.49 | 1.50 | 1.32 | 1.19 | 1.22 |
| Alanine | 7.20 | 6.25 | 6.53 | 7.63 | 7.10 | 7.08 |
| Valine | 7.38 | 6.51 | 6.98 | 6.87 | 7.48 | 7.54 |
| Isoleucine | 6.23 | 6.19 | 6.38 | 5.24 | 6.10 | 5.87 |
| Leucine | 14.98 | 14.80 | 16.51 | 22.88 | 24.45 | 23.12 |
| Tyrosine | 3.44 | 2.64 | 2.79 | 2.55 | 2.60 | 2.38 |
| Phenylalanine | 3.61 | 3.66 | 3.96 | 4.11 | 4.50 | 4.55 |
| Lysine, Total | 7.98 | 7.53 | 7.12 | 6.25 | 5.83 | 5.98 |
| Histidine | 1.81 | 1.79 | 1.86 | 1.73 | 1.76 | 1.75 |
| Arginine | 2.08 | 1.97 | 1.72 | 1.50 | 1.29 | 1.39 |
| BCAA | 28.6% | 27.5% | 29.9% | 35.0% | 38.0% | 36.5% |
| EAA | 58.8% | 59.2% | 62.2% | 67.8% | 69.9% | 69.4% |
| Protein (N = 6.4) | 79.0 | 68.7 | 69.2 | 73.1 | 72.3 | 72.8 |
| Protein (N = 6.78) | 83.7 | 72.8 | 73.3 | 77.5 | 76.6 | 77.2 |
| Calcium (mg/100 g) | 228 | 306 | 260 | 358 | 392 | 411 |
| Sodium | 3374 | 3829 | 4475 | 4015 | 2905 | 2722 |
| Potassium | 652 | 940 | 949 | 793 | 795 | 622 |
| ACE Inhibition (N = 6.4) | 6.9 | 9.1 | 8.6 | 4.2 | 4.4 | 4.0 |
| ACE Inhibition (N = 6) | 7.3 | 9.6 | 9.1 | 4.5 | 4.7 | 4.2 |
| Degree of Hydrolysis | 32.8% | 35.9% | 39.7% | 47.3% | 47.7% | 47.9% |

Examples

Example 2

Stimulation of Increased Blood Flow, Vasodilation, NO Production

Individuals were provided with 2 weeks of daily supplementation with either the peptide product of the invention, or placebo. After completion of the first 2 week supplementation period and first day of vascular testing there was an interval of 1-2 weeks, after which the individuals started the second 2 week supplementation period, each individual consuming the alternative supplement. Individuals were evaluated at four separate times during the protocol, and asked to fast for 12 hours, as well as to avoid alcohol, caffeine, and exercise for 24 hours, and to consume 36 ounces of water the night before each evaluation and an additional 12 to 16 ounces of water the morning of the visit, to ensure that each person was adequately hydrated.

The peptide product was produced by Glanbia Nutritionals, Twin Falls, Id. A single dose of 5 g was premeasured and placed in individual packets with artificial sweetener. Individuals participating in the study were provided with a 2-week supply and instructed to consume one packet per day mixed in 300 mL water.

On the morning of vascular testing, individuals consumed one packet containing 5 g of peptide product or placebo mixed in water. Fasting measurements of flow mediated dilation (FMD) and forearm blood flow (FBF) were determined. Fifteen minutes of recovery were allowed between FMD and FBF measurements prior to ingestion of the test beverage. Following these baseline measurements, subjects consumed a single 5 g dose of either peptide product or placebo mixed in 300 mL of water and artificial sweetener.

Post-ingestion FMD and FBF measurements were made intermittently. Blood samples were obtained at 15, 30, 45, 60, 90, and 120 minutes post-ingestion. Subjects rested in a comfortable position for the entire duration of the test. To ensure standardization between testing trials subjects were asked to maintain their current level of physical activity during the study period and to repeat their dietary intake from previously recorded diet records the day prior to each vascular testing visit. Flow mediated dilation (FMD) was assessed using standardized procedures for performing high-frequency ultrasonographic imaging before (PRE) and at 30, 60, and 90 min after ingestion of the test beverage. The technique provokes the release of nitric oxide, resulting in vasodilation that can be quantitated as an index of vasomotor function. All tests were performed in a quiet, temperature-controlled room after a 10 minute period in a supine position. A blood pressure cuff was placed on the upper right arm for occlusion. ECG leads were attached to monitor heart rate throughout the procedure. The brachial artery was imaged above the antecubital crease, and the transducer was placed to image the brachial artery in a longitudinal axis with clear visualization of the anterior and posterior vessel walls. When a clear image of the anterior and posterior walls of the artery was obtained, the transducer was held by a stereotactic clamp and the position held constant for the duration of the data collection. Baseline brachial artery diameter was recorded for 30 heart beats. A mark was made on the arm where the image was collected. The cuff was inflated to 200 mm Hg for 5 min using a rapid cuff inflator (Hokanson E20, Bellevue, Wash., USA) to occlude the brachial artery, and then released. Arterial diameter was then assessed continuously for 300 heart beats after occlusion. Images of the brachial artery were obtained using an Acuson 13.0-MHz linear array transducer and an Aspen cardiac ultrasound system (Acuson Carp, Elmwood Park, N.J.).

Image analysis was performed using MIA software (Medical Imaging Applications, Iowa City, Iowa, USA). For baseline, the average diameter taken from 30 frames was used. Three hundred frames were recorded for post-occlusion. Peak post-occlusion diameter was calculated by averaging the vessel diameter 5 frames immediately before the observed peak diameter and the 5 frames immediately after the same mark. Brachial artery FMD was calculated and expressed as a percentage of the baseline diameter.

Forearm blood flow was measured in the same right arm using venous occlusion strain gauge plethysmography. A calibrated indium/gallium-filled silastic strain gauge, encircled around the largest diameter of the right forearm, was connected to a plethysmograph (EC6, Hokanson, Inc., Bellevue, Wash., USA). The increase in forearm volume was measured after blocking the venous efflux by an upper arm cuff inflated to 50 mmHg by a rapid cuff inflator (Hokanson E20, Bellevue, Wash., USA) for 7 seconds during each 15-second cycle to determine resting forearm blood flow (R-FBF). This measurement was performed at rest (PRE) and 20, 50, 80, and 110 minutes after ingestion of the test beverage. The hand circulation was excluded by a wrist cuff inflated to 220 mmHg for 1 min before and during each flow evaluation. Forearm blood flow was estimated using specialized software (Noninvasive Vascular Program 3 (NIVP3), Hokanson, Bellevue, Wash., USA) which determined the slope of the change in forearm volume and recorded blood flow in terms of percent volume change per minute (%/min). Four plethysmographic measurements were averaged to obtain values for R-FBF. To determine reactive hyperemia induced forearm blood flow (RHFBF), a blood pressure cuff on the upper right arm was inflated to a pressure of 200 mmHg for 5 minutes. Upon release of the occlusion, FBF was determined as described above. This measurement was performed at rest (PRE) and 120 min after ingestion of the test beverage.

A blood sample was obtained from a left arm vein after subjects rested quietly for 10 minutes in the supine position. Serum glucose and insulin concentrations were analyzed in duplicate using a YSI glucose/lactate analyzer (YSI 2300 STAT, Yellow Springs, Ohio) and commercially available ELISA [Diagnostic Systems Laboratory (DSL), Webster, Tex.] (CV=7.0%) respectively, and used to calculate an index of insulin resistance.

Body mass remained stable over the course of the study, and there were no significant differences in systolic/diastolic blood pressure after 2 weeks of peptide supplementation. However, results demonstrated that blood vessel diameter, blood flow, and nitric oxide levels were increased as a result of ingestion of the peptide product of the invention.

Example 3

ACE Inhibition Assay

The ACE inhibition assay has been previously described by Cushman and Cheung (Cushman, D. W. and Cheung, H. S., Biochem. Pharmacol. (1971) 20: 1637). Briefly, substrate was prepared by dissolving 21.475 mg of Hip-His-Leu ("HHL," Sigma, St. Louis, Mo.) in 8 ml of phosphate buffered saline, with volume adjusted to 10 ml and final pH to 8.3. A 10% w/w solution of peptide composition was prepared using buffer as diluent. Angiotensin-converting enzyme stock solution was prepared by diluting 0.1 unit of ACE (rabbit lung, Sigma Chemical, St. Louis, Mo.) with buffer. To perform the assay, 10 microliters of sample were placed into a small glass tube with 200 µl of HHL and 70 µl of buffer. Tubes were placed in a 37° C. water bath and held for 3 minutes. Tubes were removed from the water bath and 20 µl of angiotensin-converting enzyme were added to each tube. Tubes were vortexed and returned to the water bath for 30 minutes. Tubes were then removed from the water bath and 250 µl HCl were added to stop the reaction. Acetic ether (1.5 ml) was added to each tube with a glass pipette, and tubes were again vortexed. Small tubes were independently placed into plastic 50 ml tubes to be centrifuged for 2 minutes at 2000 rpm. Tubes were removed from the centrifuge with care being taken not to disturb the ether layer. The ether layer (1 ml) was removed and placed in a small 10 ml beaker, then placed on a hot place to evaporate at approximately 100° C. To each evaporated sample, 1 ml of nanopure water was added. Absorbance was read at 228 nm with a reaction mixture containing no inhibitor as control.

What is claimed is:

1. A method for isolating leucine-rich peptides from a leucine-rich protein source, the method comprising the steps of:
   a) hydrolyzing the protein in the presence of at least one leucyl aminopeptidase without additional proteases that are not leucyl aminopeptidases to form a protein hydrolysate,
   b) deactivating the aminopeptidase(s), and
   c) filtering the protein hydrolysate to produce a permeate containing leucine-rich peptides having a leucine content of from 12 to 40 weight percent and a molecular weight of from about 200 to about 4,000 in the permeate.

2. The method of claim 1 wherein the protein source is chosen from among the group consisting of legumes, fish, meat, milk, blood, egg, corn, wheat gluten, maize, and combinations thereof.

3. The method of claim 1 wherein the step of filtering is performed to collect peptides having a molecular weight of from about 200 to about 1,000.

4. The method of claim 1 wherein the step of filtering is performed to collect peptides having a molecular weight of from about 400 to about 1,000.

5. The method of claim 1 wherein the protein source is chosen from among the group consisting of bovine milk, bovine whey, whey protein concentrates, whey protein isolates, and combinations thereof.

* * * * *